United States Patent [19]

Yamada et al.

[11] Patent Number: 5,264,353

[45] Date of Patent: Nov. 23, 1993

[54] PROCESS FOR PRODUCING L-THREONINE BY FERMENTATION

[75] Inventors: Katsushige Yamada; Hiromi Tsutsui; Kyousuke Yotsumoto; Masae Takeuchi; Makoto Shirai, all of Aichi, Japan

[73] Assignee: Toray Industries, Inc., Japan

[21] Appl. No.: 652,455

[22] Filed: Feb. 7, 1991

Related U.S. Application Data

[63] Continuation of Ser. No. 897,528, Aug. 18, 1986, abandoned.

[30] Foreign Application Priority Data

Aug. 23, 1985 [JP] Japan .................. 60-183925
Aug. 27, 1985 [JP] Japan .................. 60-42581

[51] Int. Cl.$^5$ .................. C12P 13/08; C12N 15/00; C12N 1/20
[52] U.S. Cl. .................. 435/115; 435/172.1; 435/252.8; 435/252.1; 435/873; 435/822; 435/848; 435/849
[58] Field of Search .................. 435/115, 172.1, 873, 435/822, 848, 849, 252.8, 252.1

[56] References Cited

U.S. PATENT DOCUMENTS 3,375,173 3/1968 Nishimura et al. .................. 435/115
3,893,888 7/1975 Tsuchida et al. .................. 435/115
4,329,427 5/1982 Updike et al. .................. 435/116

FOREIGN PATENT DOCUMENTS 8224684 12/1983 Japan .
0180597 9/1985 Japan .

OTHER PUBLICATIONS

Hirakawa et al, *Amino Acid Nucleic Acid*, vol. 28, 1973, pp. 124–128.
Brock, T. D., *Biology of Microorganisms*, 1979, Prentice-Hall.
Umbarger, H. E. in *Amino Acids*, Addison Wesley 1983, pp. 245–250.
Cohen, G. N. in *Amino Acids*, Addison Wesley 1983, pp. 147–151.
Lynn et al., in *Amino Acids*, Addison-Wesley 1983, pp. 173–179.
ATCC catalogue of Bacteria, 1989.
Kase et al., Agric. Biol. Chem. 41 (1), pp. 109–116, 1977.
Szentirmai et al., *J. of Bacteriol.* 1968, pp. 1672–1679, vol. 95.
Chemical Abstracts vol. 80, No. 11, Mar. 18, 1974, p. 242, Abstract No. 58409h, Columbus, Ohio, US.
Chemical Abstracts vol. 80, No. 17, Apr. 29, 1974, p. 177, Abstract No. 93041d, Columbus, Ohio.

*Primary Examiner*—Irene Marx
*Attorney, Agent, or Firm*—Austin R. Miller

[57] ABSTRACT

Microorganisms belonging to the genus Providencia or the genus Escherichia and having a resistance to isoleucine antagonist, produce L-threonine by fermentation in higher yield and in more amount of L-threonine accumulated.

2 Claims, No Drawings

PROCESS FOR PRODUCING L-THREONINE BY FERMENTATION

This application is a continuation of application Ser. No. 897,528, filed Aug. 18, 1986.

BACKGROUND OF THE INVENTION (a) Field of the Invention

This invention relates to a process for producing L-threonine by fermentation.

(b) Prior Art

There hitherto has been known that the microorganism belonging to the genus Providencia or Proteus of which the mutant requires L-isoleucine can be used as microorganisms capable of producing L-threonine by fermentation (Japanese Examined Patent Publication No. 4440/1968).

The method using the mutant having a sensitivity to antibiotic borrelidin and requiring L-methionine and L-valine has been known with respect to producing L-threonine by using certain microorganism of the genus Escherichia (Japanese Examined Patent Publication No. 6752/1976).

However, there is room for further improvement in the capability of the strains as to the amount of L-threonine accumulated and as to the yield of L-threonine from the starting materials such as glucose or fructose in the method using the microorganism above mentioned.

SUMMARY OF THE INVENTION

One object of the present invention is to provide an improved process for producing L-threonine by fermentation which can give a much higher accumulated amount and yield.

Another object of the invention is to provide an improved process using a novel mutant for producing L-threonine.

These and other objects of the invention will become more apparent in the detailed description and examples hereinafter.

These objects are attained by a process for producing L-threonine by fermentation which comprises the steps of:

(a) culturing an L-threonine producing microorganism belonging to the genus Providencia or the genus Escherichia until L-threonine is accumulated in a culture broth, said microorganism having a resistance to isoleucine antagonist and (b) recovering the accumulated L-threonine from the culture broth.

PREFERRED EMBODIMENTS

The microorganisms used in the present invention belong to the genus Providencia or the genus Escherichia. The genus is decided according to Bergy's Manual of Systematic Bacteriology Volume 1 (1984). Especially, the genus Providencia is decided according to pages 495 to 496 thereof. Moreover, the microorganisms used in the invention have a resistance to isoleucine antagonists and are capable of producing L-threonine.

In the invention, "isoleucine antagonist" means 1) a substance which can inhibit the growth of the microorganism belonging to the genus Providencia or the genus Escherichia, such an inhibition being reversed by supplement of isoleucine, or 2) a substance which can repress or inhibit the enzyme activity in the biosynthetic pathway of L-isoleucine.

Preferable examples of the isoleucine antagonists are thiaisoleucine, isoleucine hydroxamate, o-methylthreonine, β-methylthreonine, and so on. As for the isoleucine antagonist, thiaisoleucine is most preferably used.

The microorganisms used in the present invention include the strains which have at least the character having a resistance to isoleucine antagonist, even though these strains have other requirement for growth and a resistance to other chemical compounds.

In the invention, the microorganisms belonging to the genus Providencia preferably have a resistance to aspartic acid antagonist in addition to a resistance to isoleucine antagonist. In the invention, "aspartic acid antagonist" means (1) a substance which can inhibit the growth of the microorganism belonging to the genus Providencia, such as inhibition being reversed by supplement of aspartic acid, or (2) a substance which can repress or inhibit the enzyme activity in the biosynthetic pathway of L-aspartic acid. Preferable examples of the aspartic acid antagonist are D,L-aspartic acid hydroxamate, α-methylaspartic acid, β-methylaspartic acid, cysteinsulfinic acid, difluorosuccinic acid, hadasizine, and so on. Above all, D,L-aspartic acid hydroxamate is most preferably used. These characteristics effectively operate the capability of producing L-threonine.

Moreover, in the invention there may be more preferably employed microorganisms belonging to the genus Providencia which have further characteristics selected from having a resistance to α-amino-β-hydroxyvaleric acid, having an auxotrophy, which includes leaky type, for L-isoleucine or L-leucine, and having a resistance to feedback control by L-threonine, in addition to the characteristics of having a resistance to isoleucine antagonist and aspartic acid antagonist. These characteristics also effectively operate the capability of producing L-threonine. Therefore, there may be more preferably employed microorganisms which have some or all of the above mentioned characteristics.

Representative microorganisms useful for this invention are as follows:

(a) *Providencia Rettgeri* TP6-28 (FERM BP-1135)

This TP6-28 strain has a resistance to thiaisoleucine, α-amino-β-hydroxyvaleric acid and L-ethionine; and has an auxotrophy, which includes leaky type, for L-isoleucine, and requires L-leucine for the growth thereof, and was deposited with Fermentation Research Institute in Japan on Jul. 15, 1985.

(b) *Providencia Rettgeri* AXR 2G-10 (FERM BP-1138)

This AXR 2G-10 strain has a resistance to D,L-aspartic acid hydroxamate, thiaisoleucine, α-amino-β-hydroxyvaleric acid and L-ethionine; and has an auxotrophy, which includes leaky type, for L-isoleucine, and requires L-leucine for the growth thereof, and was deposited with Fermentation Research Institute in Japan on May 17, 1986.

(c) *Providencia Rettgeri* TP7-55 (FERM BP-1137)

This TP7-55 strain has a resistance to D,L-aspartic acid hydroxamate, thiaisoleucine, α-amino-β-hydroxyvaleric acid, and L-ethionine; and has an auxotrophy, which includes leaky type, for L-isoleucine, and requires L-leucine for the growth thereof, and was deposited with Fermentation Research Institute in Japan on May 17, 1986.

(d) *Escherichia Coli* M-5 (FERM BP-1136)

This M-5 strain has a resistance to thiaisoleucine; and requires L-methionine and L-valine for the growth thereof, and has a sesitivity to borrelidin, and was deposited with Fermentation Research Institute in Japan on Feb. 24, 1986.

The FERM BP numbers are the deposit number of the Fermentation Research Institute Agency of Industrial Science and Technology, at No. 1-3, Yatabe-cho, Higashi 1-chome, Tsukuba-gun, Ibaragi-ken, 305 JAPAN, from which the microorganisms with the FERM BP numbers are available to any party who requests them.

These threonine producing microorganisms can be derived as a mutant, for example, from the following parent strains;

(i) *Providencia Rettgeri* ATCC 21118

This ATCC 21118 strain requires L-isoleucine for the growth thereof and is a parent strain of *Providencia rettgeri* TP3-105 strain which has a resistance to α-amino-β-hydroxyvaleric acid and L-ethionine; and has an auxotrophy, which includes leaky type, for L-isoleucine and requires L-leucine for the growth thereof. Moreover, TP3-105 strain is a parent strain of TP6-28 strain.

(ii) *Providencia rettgeri* AHXR 7665

This AHXR 7665 strain, which has a resistance to α-amino-β-hydroxyvaleric acid, L-ethionine, and D,L-aspartic acid hydroxamate; and has an auxotrophy including leaky type for L-isoleucine and requires L-leucine for the growth thereof, is a mutant derived from TP3-105 strain, and is a parent strain of TP7-55 strain.

(iii) *Escherichia Coli* ATCC 21248

This ATCC 21248 strain requires L-methionine and L-valine for the growth thereof, and is a parent strain of *Escherichia coli* BS-58 (FERM P-1330) strain. BS-58 strain, which requires L-methionine and L-valine; and has a sensitivity to borrelidin, is a parent strain of M-5 strain.

These mutants can be relatively easily obtained by conventional mutation methods. Namely, in the case of obtaining the isoleucine antagonist resistant mutant, the parental cells are irradiated with ultraviolet light or treated with mutagene, for example, N-methyl-N'-nitro-N-nitrosoguanidine or ethylmethane sulfonate. The resistant mutant is obtained as the strain having the capability of growth, on the agar plate containing a high enough concentration of isoleucine antagonist that the parent strain can not grow.

In the invention, the microorganism having a resistance to isoleucine antagonist is defined as a strain of the microorganism which has a stronger resistance to isoleucine antagonist than the parent strain does, and is preferably defined as a strain of the microorganism whose growth degree is at least 50% in the culture medium containing so high a concentration of isoleucine antagonist, as to reduce the relative growth degree of the parent strain to less than 40%, based on the case in the absence of isoleucine antagonist. For example, in the case of a thiaisoleucine resistant strain, the microorganism having a resistance to thiaisoleucine is defined as a strain whose growth degree in the culture medium supplemented with 5 mM of thiaisoleucine is at least 50% based on the case in the absence of thiaisoleucine.

In the invention, growth degree is shown by the relative optical density of the culture broth at 660 nm when the optical density of culture broth in none-supplement of isoleucine antagonist is defined as 100%.

In the case of obtaining the aspartic acid antagonist-resistant mutant, in addition to isoleucine antagonist-resistant mutant, the parental cells are irradiated with ultraviolet light or treated with mutagene, for example, N-methyl-N'-nitro-N-nitrosoguanidine or ethylmethane sulfonate. The resistant mutant is obtained as the strain having the capability of growth on the agar plate containing high enough concentration of aspartic acid antagonist that the parent strain can not grow.

In the invention, the microorganism having a resistance to aspartic acid antagonist is defined as a strain of the microorganism which has a stronger resistance to aspartic acid antagonist than the parent strain does, and is preferably defined as a strain of the microorganism whose growth degree is at least 60% in the culture medium containing so high a concentration of aspartic acid antagonist, as to reduce the relative growth degree of the parent strain to less than 30%. In the invention, the growth degree is shown by the relative optical density of of the culture broth at 660 nm when the optical density of culture broth in none-supplement of aspartic acid antagonist is defined as 100%.

In the present invention, as a culture medium for producing L-threonine can be used a conventional medium containing carbon source, nitrogen source, inorganic ions and if necessary, other organic minor ingredients.

The preferable culture medium may contain 2 to 15% of carbon source, for example, carbohydrates such as glucose, fructose, hydrolysate of starch or cellulose, or molasses; organic acids such as fumalic acid, citric acid, or succinic acid; alcohols such as glycerol; contain 0.5 to 4.0% of nitrogen source, for example, organic ammonium salts such as ammonium acetate, urea inorganic ammonium salts such as ammonium sulfate, ammonium chloride, ammonium phosphate, or ammonium nitrate; ammonia gas; aqueous ammonia; contain 0.001 to 0.4% of required materials such as L-valine, L-isoleucine, or L-leucine as an organic nutrient; and if necessary, contain 0 to 4% of corn steep liquor, polypeptone, or yeast extract and the like as an organic minor ingredient. In addition, a small amount of potassium phosphate, magnesium sulfate, ferrous sulfate 7-hydrate, and 4- to 6-hydrate of manganese sulfate, etc. may be added to the culture medium as an inorganic ion.

Cultivation is carried out preferably under aerobic conditions. Preferable result can be obtained by adjusting the pH of the medium to from 5 to 9 and controlling a temperature from 24° to 37° C. during cultivation, and by shaking or stirring with aeration for from 48 to 120 hours.

The recovery of accumulated L-threonine from the culture broth is carried out by conventional methods. For example, the culture broth from which the cells are removed is adjusted to pH 2 with hydrochloric acid. Then, the broth solution is passed through the strongly acidic ion exchange resin, and the adsorbant is eluted by dilute aqueous ammonia, Thereafter ammonia is evaporated from the resulting eluent, and then the resulting solution is condensed. Alcohol is added to the resultant, the crystals formed under cooling are collected, and then L-threonine can be obtained.

The invention will be more clearly understood with reference to the following Experiments and Examples.

However, these Experiments and Examples are intended to illustrate the invention and are not to be construed as limiting the scope of the invention.

EXPERIMENT 1

Isolation of the Thiaisoleucine-Resistant Mutants Belonging to the Genus Providencia The cells of *Providencia rettgeri* TP3-105 and the cells of *Providencia rettgeri* AHXR 7665 were mutagenized by N-methyl-N'-nitro-N-nitrosoguanidine treatment (300 μg/ml, for 10 min, at 30° C.) according to a conventional method. The resulting cells were spread on the agar plate which has the following composition.

| Medium composition for agar plate | |
|---|---|
| Glucose | 0.5% |
| (NH$_4$)$_2$SO$_4$ | 0.1% |
| K$_2$HPO$_4$ | 0.7% |
| KH$_2$PO$_4$ | 0.3% |
| MgSO$_4$.7H$_2$O | 0.01% |
| D,L-thiaisoleucine | 0.15% |
| L-leucine | 0.2% |
| L-valine | 0.2% |

Then, after incubation for 5 to 7 days at 30° C., large colonies formed on the plate were picked up, and thiaisoleucine resistant mutants, *Providencia rettgeri* TP6-28 strain and TP7-55 strain were respectively obtained.

EXPERIMENT 2

Isolation of the Thiaisoleucine Resistant Mutant Belonging to the Genus Escherichia The cells of *Escherichia coli* BS-58 were mutagenized by N-methyl-N'-nitro-N-nitrosoguanidine treatment (300 μg/ml, for 10 min, at 30 ° C.) according to a conventional method. The resulting cells were spread on the agar plate which has the following composition.

| Medium composition for agar plate | |
|---|---|
| Glucose | 0.5% |
| (NH$_4$)$_2$SO$_4$ | 0.1% |
| K$_2$HSO$_4$ | 0.7% |
| KH$_2$SO$_4$ | 0.3% |
| MgSO$_4$.7H$_2$O | 0.01% |
| L-methionine | 0.01% |
| D,L-thiaisoleucine | 0.15% |
| L-leucine | 0.2% |
| L-valine | 0.2% |

Then, after incubation for 5 to 7 days at 30° C., large colonies formed on the plate were picked up, and thiaisoleucine resistant mutant, *Escherichia coli* M-5 strain was obtained.

EXPERIMENT 3

Degree of Resistance of the Thiaisoleucine Resistant Nutants Belonging to the Genus Providencia Each strain shown in Table 1 was cultivated in bouillon liquid at 30° C. for 16 hours with shaking, and the grown cells were harvested and washed with physiological saline.

The resulting cell suspension was inoculated into 5 ml of the following minimal medium containing 0 mM, 2.5 mM, 5.0 mM, and 10 mM of thiaisoleucine, respectively, and cultivated at 30° C. for 24 hours, and the growth degree of each strain was measured.

| Minimal medium composition | |
|---|---|
| Glucose | 0.5% |
| (NH$_4$)$_2$SO$_4$ | 0.1% |
| K$_2$HPO$_4$ | 0.7% |
| KH$_2$PO$_4$ | 0.3% |
| MgSO$_4$.7H$_2$O | 0.01% |
| L-isoleucine | 0.001% |
| L-leucine | 0.05% |
| L-valine | 0.05% |

The results were shown in Table 1.

TABLE 1

| | Relative growth degree*) (%) Concentration of thiaisoleucine added (mM) | | | |
|---|---|---|---|---|
| Strains | 0 | 2.5 | 5.0 | 10.0 |
| Parental strain | | | | |
| Providencia rettgeri TP3-105 | 100 | 65.0 | 37.8 | 10.5 |
| Providencia rettgeri TP6-28 | 100 | 90.6 | 82.3 | 73.5 |
| Providencia rettgeri AKR2G-10 | 100 | 95.1 | 94.4 | 83.3 |
| Providencia rettgeri TP7-55 | 100 | 92.0 | 94.9 | 93.4 |

*)Relative growth degree is shown by the relative optical density of the culture broth at 660 nm when the optical density of the culture broth in the absence of thiaisoleucine is 100%.

The growth of the thiaisoleucine resistant mutants, *Providencia rettgeri* TP6-28 strain, AXR 2G-10 strain and TP7-55 strain used in the present invention, were not inhibited by thiaisoleucine compared with that of parental strain *Providencia rettgeri* TP3-105 strain. Therefore, it is evident that these mutants have a resistance to thiaisoleucine.

EXPERIMENT 4

Degree of Resistance of the Thiaisoleucine Resistant Mutant Belonging to the Genus Escherichia Each strain shown in Table 2 was cultivated in bouillon liquid at 30° C. for 16 hours with shaking, and the grown cells were harvested and thoroughly washed with physiological saline.

The resulting cell suspension was inoculated into 5 ml of the following minimal medium containing mM, 5 mM, 10 mM of thiaisoleucine, respectively, and cultivated at 30° C. for 24 hours, and the growth degree of each strain was measured.

| Minimal medium composition | |
|---|---|
| Glucose | 0.5% |
| (NH$_4$)$_2$SO$_4$ | 0.1% |
| K$_2$HPO$_4$ | 0.7% |
| KH$_2$PO$_4$ | 0.3% |
| MgSO$_4$.7H$_2$O | 0.01% |
| L-methionine | 0.01% |
| L-valine | 0.01% |

The results were shown in Table 2.

TABLE 2

| | Relative growth degree*) (%) Concentration of thiaisoleucine added (mM) | | |
|---|---|---|---|
| | 0 | 5 | 10 |
| Parental strain | | | |
| Escherichia coli BS-58 | 100 | 0.51 | 0.34 |
| Escherichia coli | 100 | 102 | 67.9 |

TABLE 2-continued

| | Relative growth degree*) (%) Concentration of thiaisoleucine added (mM) | | |
|---|---|---|---|
| | 0 | 5 | 10 |
| M-5 | | | |

*)Relative growth degree is shown by the relative optical density of the culture broth at 660 nm when the optical density of the culture broth in the absence of thiaisoleucine is 100%.

The growth of the thiaisoleucine resistant mutant *Escherichia coli* M-5 strain used in the present invention, is not inhibited by thiaisoleucine compared with that of parental strain *Escherichia coli* BS-58 strain. Therefore, it is evident that this mutant has a resistance to thiaisoleucine.

EXPERIMENT 5

Isolation of the Mutant Strain having a Resistance to D,L-Aspartic Acid Hydroxamate The cells of *Providencia rettgeri* TP6-28 and the cells of *Providencia rettgeri* TP3-105 were mutagenized by N-methyl-N'-nitro-N-nitrosoguanidine treatment (300 μg/ml, for 10 min, at 30° C.) according to a conventional method. The resulting cells were spread on the agar plate which has the following composition.

| Medium composition for agar plate | |
|---|---|
| Glucose | 0.5% |
| (NH$_4$)$_2$SO$_4$ | 0.1% |
| K$_2$HPO$_4$ | 0.7% |
| KH$_2$PO$_4$ | 0.3% |
| MgSO$_4$.7H$_2$O | 0.01% |
| L-isoleucine | 0.005% |
| L-leucine | 0.005% |
| D,L-aspartic acid hydroxamate | 2 g/l |

Then, after incubation for 5 to 8 days at 30° C., large colonies formed on the plate were picked up, and D,L-aspartic acid hydroxamate resistant mutants, *Providencia rettgeri* AXR 2G-10 strain and AHXR 7665 strain, were respectively obtained.

EXPERIMENT 6

Degree of Resistance of D,L-Aspartic Acid Hydroxamate Resistant Mutants

Each strain shown in Table 3 was cultivated in bouillon liquid at 30° C. for 16 hours with shaking, and grown cells were harvested and washed with physiological saline.

The resulting cell suspension was inoculated into 5 ml of the following minimal medium containing 0 g/l, 0.25 g/l, 0.5 g/l, 1.0 g/l, 2.0 g/l of D,L-aspartic acid hydroxamate, respectively, and cultivated at 30° C. for 24 hours, and the growth degree of each strain was measured.

| Minimal medium composition | |
|---|---|
| Glucose | 0.5% |
| (NH$_4$)$_2$SO$_4$ | 0.1% |
| K$_2$HPO$_4$ | 0.7% |
| KH$_2$PO$_4$ | 0.3% |
| MgSO$_4$.7H$_2$O | 0.01% |
| L-isoleucine | 0.005% |
| L-leucine | 0.005% |

The results are shown in Table 3.

TABLE 3

| | Relative growth degree*) (%) Amount of D,L-aspartic acid hydroxamate added (g/l) | | | | |
|---|---|---|---|---|---|
| | 0 | 0.25 | 0.5 | 1.0 | 2.0 |
| Parental strain | | | | | |
| *Providencia rettgeri* TP3-105 | 100 | 1.9 | 0.7 | 0.4 | 0.9 |
| *Providencia rettgeri* AXR 2G-10**) | 100 | 85.8 | 67.6 | 55.0 | 1.9 |
| *Providencia rettgeri* TP7-55***) | 100 | 83.4 | 68.0 | 56.0 | 38.4 |

*)Relative growth degree is shown by the relative optical density of the culture broth at 660 nm when the optical density of the culture broth in the absence of D,L-aspartic acid hydroxamate is 100%.
**)*Providencia rettgeri* AXR 2G-10 strain was derived from TP6-28 strain according to Experiment 1.
***)*Providencia rettgeri* TP7-55 strain was derived from AHXR 7665 strain according to Experiment 5.

The growth of D,L-aspartic acid hydroxamate resistant mutants *Providencia rettgeri* AXR 2G-10 strain and TP7-55 strain used in the present invention were not inhibited in the presence of high concentration of D,L-aspartic acid hydroxamate compared with that of parental strain TP3-105 strain. Therefore, it is evident that these mutant have a strong resistance to D,L-aspartic acid hydroxamate.

EXAMPLE 1

50 ml of fermentation medium consisting of the following composition in 1 l conical flask was sterilized at 115° C. for 10 minutes.

| Fermentation medium composition | |
|---|---|
| Glucose (sterilized separately) | 8% |
| (NH$_4$)$_2$SO$_4$ | 2.5% |
| KH$_2$PO$_4$ | 0.1% |
| MgSO$_4$.7H$_2$O | 0.04% |
| Fe$^{++}$ | 2 ppm |
| Mn$^{++}$ | 2 ppm |
| L-isoleucine | 0.005% |
| L-leucine | 0.08% |
| CaCO$_3$ (sterilized separately) | 4% |
| pH | 7.0 (neutralized with KOH) |

Each strain shown in Table 4 was cultivated at 30° C. for 16 hours with shaking in bouillon liquid. 5 ml of the resulting culture broths were put into the fermentation medium, and then cultivation was carried at 30° C. for 90 hours with shaking condition of 110 rpm and 5 cm-stroke.

After cultivation, the amount of L-threonine in the filtrate which was obtained by removing the cells and calcium carbonate from the culture broth was quantitatively analyzed by automatic amino acid analyzer (produced by Japan Electric Co. JLC-200A) and the results shown in Table 4 were obtained

TABLE 4

| | Strains | Amount of L-threonine accumulated (g/l) | Yield of*) L-threonine produced (%) |
|---|---|---|---|
| Comparative example | *Providencia rettgeri* TP3-105 | 12.9 | 17.2 |
| Example | *Providencia rettgeri* TP6-28 | 20.4 | 24.8 |
| Example | *Providencia rettgeri* AXR 2G-10 | 23.4 | 29.2 |

TABLE 4-continued

| Strains | Amount of L-threonine accumulated (g/l) | Yield of*) L-threonine produced (%) |
|---|---|---|
| Providecia rettgeri TP7-55 | 22.0 | 28.0 |

*)Yield of L-threonine produced was based on the consumed glucose.

Both amount of L-threonine accumulated and yield of L-threonine produced were obviously improved in Examples, *Providencia rettgeri* TP6-28 strain, AXR 2G-10 strain and TP-7-55 strain.

EXAMPLE 2

Each strain shown in Table 5 was cultivated in bouillon liquid medium at 30° C. for 16 hours with shaking, and this culture broth was inoculated by 10% by volume into a small glass jar fermentor containing 800 ml of the same fermentation medium as used in Example 1 except that 0.5% of $(NH_4)_2SO_4$ and 4.0% of glucose were used. Cultivation with aeration (1 vvm) and agitation (800 rpm) was started at 30° C.

The pH and feed of nitrogen source were controlled with 25% aqueous ammonia and pH was kept from 6.5 to 8.0. Cultivation was carried out with intermittent feeding of glucose, $KH_2PO_4$, $MgSO_4$ $7H_2O$, L-leucine and L-isoleucine for 64 hours and the results shown in Table 5 were obtained.

TABLE 5

| | | Amount of L-threo-nine accumu-lated (g/l) | Yield of L-threo-nine accumu-lated (%) | Amount of alanine accumu-lated (g/l) | Amount of valine accumu-lated (g/l) |
|---|---|---|---|---|---|
| Comparative example | Providencia rettgeri TP3-105 | 39.0 | 22.5 | 4.5 | 6.6 |
| Example | Providencia rettgeri TP6-28 | 72.5 | 29.7 | 5.0 | 7.0 |
| | Providencia rettgeri AXR 2G-10 | 50.0 | 33.3 | 2.0 | ND* |
| | Providecia rettgeri TP7-55 | 72.0 | 38.0 | 4.0 | 8.0 |

*)not detected

The cells were removed from the culture broth of *Providencia rettgeri* TP6-28. 500 ml of the resulting filtrate was passed through the column packed with strong cation exchange resin DIAION (Trade Name) SKILL.1B (H type). Then, the column was washed with water and thereafter the adsorbant in the column was eluted by 2N aqueous ammonia The eluent was concentrated under reduced pressure after decolorizing.

Ethanol was added to the resultant and left standing under cooling, and then the crystals formed were collected, dried to give 32.3 g of L-threonine having over 96% of purity.

EXAMPLE 3

After each strain shown in Table 6 was cultivated in bouillon liquid medium at 30° C. for 16 hours with shaking the resulting culture broth was put into a 1 l conical flask which was charged with 40 ml of fermentation medium consisting of the following composition, and which was sterilized at 115° C. for 10 minutes beforehand.

| Fermentation medium composition | |
|---|---|
| Glucose (sterilized separately) | 5% |
| $(NH_4)_2SO_4$ | 1% |
| $KH_2PO_4$ | 0.05% |
| $K_2HPO_4$ | 0.05% |
| $MgSO_4.7H_2O$ | 0.05% |
| $Fe(SO_4)_3.6H_2O$ | 0.01% |
| D,L-Methionine | 0.006% |
| L-Valine | 0.04% |
| $CaCO_3$ (sterilized separately) | 1% |
| pH | 6.8 (neutralized with KOH) |

Cultivation was carried out at 30° C. for hours with shaking conditions of 110 rpm and 5 cm-stroke. After cultivation, the amount of L-threonine in the filtrate which was obtained by removing the cells and calcium carbonate the from culture broth was quantitatively analyzed by automatic amino acid analyzer (produced by Japan Electric Co. JLC-200A), and the results shown in Table 6 were obtained.

TABLE 6

| | Strain | Amount of L-threonine accumulated (g/l) | Yield of*) L-threonine produced (g/l) |
|---|---|---|---|
| Comparative Example | Escherichia coli BS-58 | 6.0 | 12.4 |
| Example | Escherichia coli M-5 | 8.9 | 18.3 |

*)Yield of L-threonine produced was based on the consumed glucose.

Both amounts of L-threonine accumulated and yield of L-threonine produced were obviously improved in Example, *Escherichia coli* M-5. The cells were removed from the culture broth of *Escherichia coli* M-5. 200 ml of the resulting filtrate was passed through the column packed with strong cation exchange resin DIAION (Trade Name) SK.1B (H type). Then, the column was washed with water and thereafter the adsorbant in the column was eluted by 2N aqueous ammonia The eluent was concentrated under reduced pressure after decolorizing Ethanol was added to the resultant and left standing under cooling, and then the crystals formed were collected, dried to give 1.55 g of L-threonine having over 96% of purity.

What we claim is:

1. A process for producing L-threonine by fermentation which comprises the steps of:
   (a) culturing a microorganism selected from the group consisting of *Providencia rettgeri* FERM BP-1135 (TP-6-28), *Providencia rettgeri* FERM BP-1137 (TP-7-55) and *Providencia rettgeri* FERM BP-1138 (AXR 2G-10) in an aqueous nutrient medium containing assimilable sources of carbon, nitrogen and inorganic substances; and (b) recovering the accumulated L-threonine from the culture broth.

2. A process for producing L-threonine by fermentation which comprises the steps of:
  (a) culturing *Escherichia coli* FERM BP-1136 (M-5) in an aqueous nutrient medium containing assimilable sources of carbon, nitrogen and inorganic substances; and
  (b) recovering the accumulated L-threonine from the culture broth.

* * * * *

UNITED STATES PATENT AND TRADEMARK OFFICE
CERTIFICATE OF CORRECTION

PATENT NO. : 5,264,353
DATED : November 23, 1993
INVENTOR(S) : Katsushige Yamada et al It is certified that error appears in the above-indentified patent and that said Letters Patent is hereby corrected as shown below:

Column 6, after line 19, add a separating line the entire length of Table 1.

Column 6, line 45, please change "mM" to --0 mM--.

Column 6, after line 67, add a separating line the entire length of Table 2.

Column 8, after line 8, add a separating line the entire length of Table 3.

Column 8, line 30, please change "1 (" to --1 ℓ--.

Column 9, line 29, please change "MgSO₄ 7H₂O" to --MgSO₄·7H₂O--.

Column 9, line 60, please change "SKILL.1B" to --SK·1B--.

Column 10, line 23, after "for" insert --72--.

Signed and Sealed this

Twenty-second Day of November, 1994

Attest:

BRUCE LEHMAN

Attesting Officer    Commissioner of Patents and Trademarks